(12) United States Patent
Yang

(10) Patent No.: US 9,645,125 B2
(45) Date of Patent: May 9, 2017

(54) VACUUM CHAMBER MEASUREMENT USING RESIDUAL GAS ANALYZER

(71) Applicant: INFICON, Inc., East Syracuse, NY (US)

(72) Inventor: Chenglong Yang, Fremont, CA (US)

(73) Assignee: INFICON, INC., East Syracuse, NY (US)

( * ) Notice: Subject to any disclaimer, the term of this patent is extended or adjusted under 35 U.S.C. 154(b) by 296 days.

(21) Appl. No.: 14/096,900

(22) Filed: Dec. 4, 2013

(65) Prior Publication Data
US 2014/0157863 A1 Jun. 12, 2014

Related U.S. Application Data

(60) Provisional application No. 61/734,205, filed on Dec. 6, 2012.

(51) Int. Cl.
*G01N 7/00* (2006.01)
*G01N 33/00* (2006.01)

(52) U.S. Cl.
CPC .................. *G01N 33/0009* (2013.01)

(58) Field of Classification Search
CPC ........... G01N 33/0009; G01N 33/0004; G01N 33/0036; G01N 1/24; G01N 27/127
USPC ....................................................... 73/23.2
See application file for complete search history.

(56) References Cited

U.S. PATENT DOCUMENTS

| | | | |
|---|---|---|---|
| 4,692,630 A | 9/1987 | Gogol | |
| 4,988,871 A | 1/1991 | Gogol | |
| 5,261,976 A * | 11/1993 | Schultz | .................... C21D 1/76 148/508 |
| 5,808,308 A | 9/1998 | Holkeboer | |
| 5,850,084 A | 12/1998 | Holkeboer | |
| 5,889,281 A | 3/1999 | Holkeboer et al. | |
| 6,286,362 B1 * | 9/2001 | Coffman | ............... G01M 3/202 73/40.7 |
| 6,468,814 B1 | 10/2002 | Frees et al. | |
| RE38,138 E | 6/2003 | Holkeboer et al. | |
| 6,642,641 B2 | 11/2003 | Ellefson et al. | |
| 6,740,195 B2 | 5/2004 | Frees et al. | |
| 7,041,984 B2 | 5/2006 | Ellefson et al. | |
| 7,257,494 B2 | 8/2007 | Conner et al. | |
| 2002/0153820 A1 | 10/2002 | Ellefson et al. | |
| 2003/0008422 A1 | 1/2003 | Frees et al. | |

(Continued)

*Primary Examiner* — Eric S McCall
*Assistant Examiner* — Mohammed E Keramet-Amircolai
(74) *Attorney, Agent, or Firm* — Barclay Damon, LLP

(57) ABSTRACT

A method of measuring an atmosphere in a guest vacuum chamber of a vacuum tool includes measuring a first composition of the atmosphere in the host vacuum chamber using a residual gas analyzer (RGA). The host and guest vacuum chambers are not coupled during the measuring of the first composition. The host vacuum chamber is coupled to the guest vacuum chamber, so the atmospheres in each can mix in the host vacuum chamber. A second composition of the atmosphere in the host vacuum chamber is measured using the RGA after the chambers are coupled. Using a processor, a composition of the guest atmosphere is automatically determined using the measured first and second compositions. A vacuum tool can include the host and guest chambers, the valve, the RGA, and a processor configured to control the valve to carry out this or other methods.

20 Claims, 5 Drawing Sheets

(56) References Cited

U.S. PATENT DOCUMENTS

| | | | |
|---|---|---|---|
| 2003/0230322 A1* | 12/2003 | Hillman | C23C 16/4408 134/11 |
| 2005/0205256 A1* | 9/2005 | DiFoggio | E21B 49/08 166/250.16 |
| 2005/0256653 A1 | 11/2005 | Conner et al. | |
| 2005/0258374 A1 | 11/2005 | Ellefson et al. | |
| 2009/0014644 A1 | 1/2009 | Yang et al. | |
| 2010/0223979 A1* | 9/2010 | Ploehn | G01N 15/0826 73/38 |
| 2011/0236569 A1* | 9/2011 | Weiller | B23K 26/123 427/162 |

* cited by examiner

VACUUM CHAMBER MEASUREMENT USING RESIDUAL GAS ANALYZER

CROSS-REFERENCE TO RELATED APPLICATIONS

This application is a nonprovisional claiming the benefit of U.S. Provisional Patent Application Ser. No. 61/734,205, filed Dec. 6, 2012 and entitled "Using Residual Gas Analyzer For Vacuum Chamber Leak Detection," the entirety of which is incorporated herein by reference.

TECHNICAL FIELD

The present application relates to measuring gas concentrations or gas partial pressures in chambers, e.g., vacuum chambers used in semiconductor processing.

BACKGROUND

The process of making semiconductors, e.g., integrated-circuit transistors, involves numerous processes carried out under very low pressures. These pressures are maintained in what are commonly referred to as "vacuum chambers." In general, a vacuum chamber is an enclosure connected to a pumping system, e.g., one including a cryo pump or turbo pump. The pumping system maintains low or extremely low pressures, e.g., $10^{-8}$ Torr for a base pressure or 5 mTorr during processing. The pumping system can maintain specified concentrations of selected gases in the chamber. A "vacuum tool" is a device that includes one or more vacuum chamber(s) and facilities to transfer workpieces in and out of the vacuum chamber(s). An example of a vacuum tool, specifically a cluster tool, is the ENDURA physical vapor deposition (PVD) machine made by APPLIED MATERIALS. For example, PVD processes for depositing copper (Cu) and tantalum nitride (Ta(N)) require vacuum, e.g., ~5 mTorr. Throughout this disclosure, "vacuum" refers to pressures much lower than atmospheric (1 atm =760 Torr), e.g., <20 Torr.

Rate-of-rise (ROR) is one of the simplest tools to help monitor the health of the vacuum system. An ROR curve (or "relapse curve") can be obtained by pumping the system to the pre-selected pressure (base pressure) and then closing the vacuum valve and monitoring the pressure as a function of time. The ROR curve provides a measure of the gas loads that can be easily compared to a "standard" previously obtained curve for a given system.

The ROR curve can be produced by pumping down for at least ten minutes then closing all valves to isolate the chamber to be tested. No pumping is performed for 2 to 3 minutes of testing. The pressure in the chamber is plotted over time. In an example, <=2000 nTorr/min. is an acceptable rate of rise; more than that indicates a need for corrective action. Pressure increase can result from outgassing from moisture or other materials in the chamber, e.g., materials such as hydrocarbons coating the surface of the chamber or process kits. Pressure increase can also result from leaks between the chamber and the outside atmosphere, or between the chamber and its pumping or other components. For example, a leak in a cutoff valve can leak process gases, e.g., nitrogen ($N_2$) or argon (Ar), into the chamber. Particulates in the valve can mechanically block it from closing fully, e.g., particulates from chemical vapor deposition (CVD) systems (e.g., FIG. 2). Failures to close can also be a result of valve end-of-life. Gas leaks can also result from failures of mass flow controllers (MFCs) upstream of the final cutoff valve.

Many semiconductor fabrication plants ("fabs") perform ROR testing on each chamber to qualify that chamber before using it to produce silicon wafers. Even if multiple chambers are tested simultaneously, this can take a considerable amount of time, e.g., from tens of minutes to hours per chamber. ROR testing must be repeated periodically, e.g., daily or once every 2 to 3 days, increasing the time consumed. Wafers cannot be run during ROR testing, reducing fab throughput. ROR testing can also not notify operators of failures that occur between ROR tests. Since a 300 mm wafer can cost thousands of dollars, early detection of failures can greatly improve the economic viability of a fab. In addition, the measured ROR curve can reflect a variety of failure modes, not all of which can be distinguished on the basis of ROR testing alone. For example, a pressure increase because of $N_2$ ingress could be a process-gas leak or an outside-air leak. Other pressure increases could be from leaks or outgassing. An ROR failure can therefore require further time-consuming testing to determine the cause of a failure. In some schemes, ROR testing is repeated if a failure is indicated. This can require an additional 30 minute delay and repeated pumpdown. There is, therefore, a need for an improved way of testing chambers.

Various fabs use residual gas analyzers (RGAs) to test chambers. RGAs perform mass spectroscopy on molecules in chambers to determine the composition of those molecules or their partial pressures. Various schemes install an RGA on each process chamber to replace ROR testing. However, this requires a large amount of equipment. There is, therefore, a need for a way of testing multiple chambers with less equipment. Some systems use RGAs on transfer chambers to provide in-situ air leak detection for PVD chambers. However, owing to dynamic pressure changes in short time periods (e.g. less than 10 seconds) during wafer transfer, these systems have performance limitations that can prevent them from being used in place of the ROR test in production. For example, some systems are not sensitive enough to detect leaks in nitritation chambers such as Ta(N) or TiN PVD that involve $N_2$ processing. In addition, these systems do not provide detection of leaks in process chambers attached to the buffer chamber. Moreover, if the process recipe calls for multiple process chambers to be open at once, it can be difficult to determine the atmospheres in each chamber independently. Likewise, pressure transients during wafer moving or interference from other actions by the tool can decrease the accuracy of such measurements. As used herein, "measuring a chamber" can include measuring the pressure in a chamber, partial pressures of various gases, or composition of the atmosphere in a chamber, or testing for or detecting leaks.

BRIEF DESCRIPTION

According to an aspect, there is provided a method of measuring an atmosphere in a guest vacuum chamber, the method comprising receiving a vacuum tool having the guest vacuum chamber selectively couplable to a host vacuum chamber, measuring a first composition of the atmosphere in the host vacuum chamber using a residual gas analyzer (RGA) when the host and guest vacuum chambers are not coupled, coupling the host vacuum chamber to the guest vacuum chamber, so that the atmosphere in the host vacuum chamber mixes with the atmosphere in the guest vacuum chamber to form a mixed atmosphere in the host vacuum chamber, measuring a second composition of the mixed atmosphere in the host vacuum chamber using the RGA after the chambers are coupled, and using a processor, automatically determining a composition of the atmosphere in the guest vacuum chamber using the measured first and second compositions.

The method can include pumping down the host vacuum chamber after measuring the second composition. The method can include mechanically moving a component within the host vacuum chamber or the guest vacuum chamber while the host vacuum chamber is coupled to the guest vacuum chamber. The method can include automatically waiting a selected time between the coupling step and the measuring-second-composition step using the processor. The method can include pumping the host vacuum chamber down to a selected pressure and concurrently measuring the first composition of the atmosphere in the host vacuum chamber using the RGA. The method can include receiving a command input from a host interface and performing the measuring-first-composition, coupling, measuring-second-composition, and determining steps in response to the received command input. The vacuum tool can include a plurality of guest vacuum chambers and the method can include receiving a command input and an indication of one of the plurality of guest vacuum chambers from an equipment controller and performing the measuring-first-composition, coupling, measuring-second-composition, and determining steps in response to the received command input, the coupling step including coupling the indicated one of the guest vacuum chambers to the host vacuum chamber. The coupling step can include coupling the chambers for at least 15 seconds.

According to another aspect, there is provided a vacuum tool. The vacuum tool comprises a first host vacuum chamber, a first guest vacuum chamber, a first valve operative to selectively couple the first host vacuum chamber and the first guest vacuum chamber, a first residual gas analyzer (RGA) configured to measure composition of an atmosphere in the first host vacuum chamber, and a processor configured to automatically operate the valve to decouple the first chambers, measure a first composition of the atmosphere in the first host vacuum chamber using the first RGA, operate the valve to couple the chambers, measure a second composition of the atmosphere in the first host vacuum chamber using the first RGA, and determine a composition of an atmosphere in the first guest vacuum chamber using the measured first and second compositions of the atmosphere in the second host vacuum chamber .

The tool can include one or more lift pins arranged in the first guest vacuum chamber and the processor can be further configured to move the lift pins while the chambers are coupled. The tool can include a second host vacuum chamber, a second guest vacuum chamber, a second valve operative to selectively couple the second host vacuum chamber to the second guest vacuum chamber, and a second RGA configured to measure composition of an atmosphere in the second host vacuum chamber, and the processor can be further configured to automatically operate the second valve to decouple the second host chamber and the second guest chamber, measure a first composition of the atmosphere in the second host vacuum chamber using the second RGA, operate the second valve to couple the second host chamber and the second guest chamber, measure a second composition of the atmosphere in the second host vacuum chamber using the second RGA, and determine a composition of an atmosphere in the second guest vacuum chamber using the measured first and second compositions of the atmosphere in the second host vacuum chamber. The tool can include a second guest vacuum chamber and a second valve operative to selectively couple the host vacuum chamber and the second guest vacuum chamber, and the processor can be configured to operate the first valve and the second valve so that only one of the first guest vacuum chamber and the second guest vacuum chamber is coupled to the first host vacuum chamber at any given time. The first or second host chamber can include a plurality of workcells. The first or second RGA can be an open ion source RGA or a closed ion source RGA. The first or second valve can be a slit valve. The tool can include a memory coupled to the processor and storing a recipe for measurements, and the processor can be further configured to sequence through the stored recipe to determine the composition of the atmosphere in the guest vacuum chamber.

Various aspects herein advantageously permit testing or measuring guest chambers using an RGA in a host chamber. This reduces the cost and complexity of a vacuum tool compared to prior tools that use multiple RGAs. This also increases the sensitivity of measurement compared to prior tools using ROR tests.

BRIEF DESCRIPTION OF THE DRAWINGS

The above and other objects, features, and advantages of the present invention will become more apparent when taken in conjunction with the following description and drawings wherein identical reference numerals have been used, where possible, to designate identical features that are common to the figures, and wherein.

The attached drawings are for purposes of illustration and are not necessarily to scale.

DETAILED DESCRIPTION

In the following description, some aspects will be described in terms that would ordinarily be implemented as software programs. Those skilled in the art will readily recognize that the equivalent of such software can also be constructed in hardware, firmware, or micro-code. Because data manipulation algorithms and systems are well known, the present description will be directed in particular to algorithms and systems forming part of, or cooperating more directly with, systems and methods described herein. Other aspects of such algorithms and systems, and hardware or software for producing and otherwise processing the signals involved therewith, not specifically shown or described herein, are selected from such systems, algorithms, components, and elements known in the art. Given the systems and methods as described herein, software not specifically shown, suggested, or described herein that is useful for implementation of any aspect is conventional and within the ordinary skill in such arts.

Figure 1:
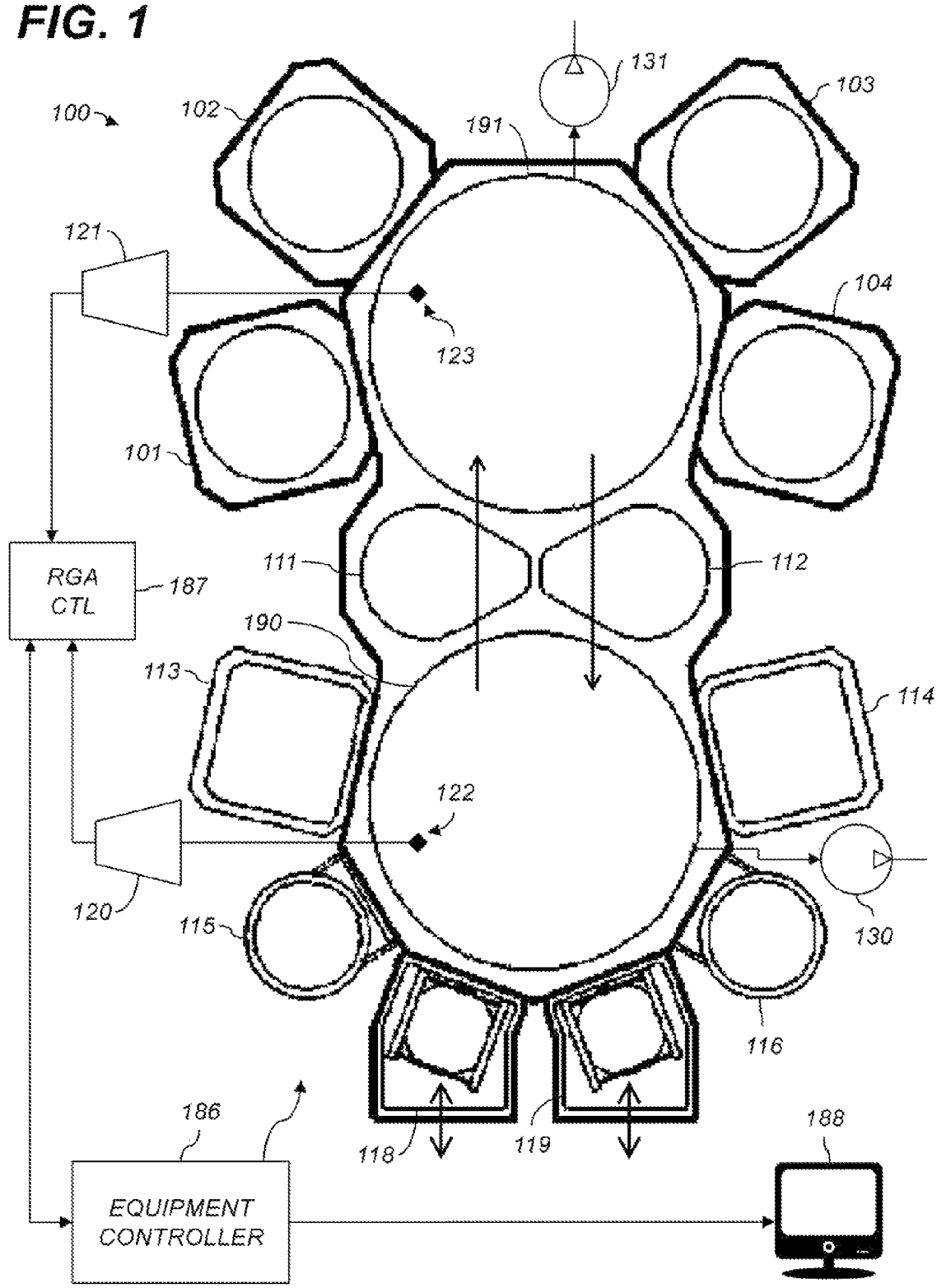
FIGS. 1 and 2 show cluster tools according to various aspects.

FIG. 1 shows an exemplary cluster tool 100 having two load-locks 118, 119. The cluster tool is an example of a vacuum tool. As indicated by the arrows, silicon wafers or other substrates (all referred to herein as "wafers") pass into and out of the tool through the load-locks 118, 119, which are chambers. Various operations are performed on the wafers in chambers 101, 102, 103, 104, 113, 114, 115, and 116. Wafers are transferred between these chambers by robotic arms or other actuators in buffer chamber 190 and transfer chamber 191. Wafers are transferred between buffer chamber 190 and transfer chamber 191 through chambers 111 and 112, as indicated by the arrows through chambers 111, 112. In various aspects, pumps 130 and 131 (e.g., vacuum pumps) maintain buffer chamber 190 and transfer chamber 191, respectively, at extremely low pressure during operation, e.g. less than $10^{-5}$ Torr, less than $10^{-6}$ Torr, or less than $10^{-7}$ Torr.

RGAs 120, 121 are configured to measure the atmosphere in buffer chamber 190 and transfer chamber 191, respectively. Each RGA 120, 121 has a respective measurement probe 122, 123 in the corresponding chamber 190, 191. RGAs 120, 121 can be, e.g., as described in U.S. Pat. No. 6,091,068, incorporated herein by reference. RGAs by INFICON can be used, e.g., INFICON TRANSPECTOR 2, TRANSPECTOR XPR3 or TRANSPECTOR CPM.

In various aspects, at least one of the RGAs 120, 121 is an open ion source RGA. Open ion source RGAs can be used, e.g., in high-vacuum chambers pressurized to less than about $10^{-5}$ Torr or less than about $10^{-6}$ Torr. Such chambers can be maintained at high vacuums during normal operation, or can be pumped down to high vacuum before operating the RGA. In other aspects, at least one of the RGAs 120, 121 is a closed ion source RGA. Closed ion source RGAs can be used at higher pressures, e.g., about 100 mTorr-2 Torr. Open and closed ion source RGAs are discussed below.

Equipment controller 186 controls the operation of the cluster tool 100 and its chambers 101, 102, 103, 104, 111, 112, 113, 114, 115, 116, 118, 119, 190, and 191, pump 130, and gas supply 135 to carry out a recipe. A "recipe" is a sequence of wafer movements and operations to be performed when a wafer is in a specific chamber. Examples of recipes are given in Herrmann et al, "Evaluating the Impact of Process Changes on Cluster Tool Performance", *IEEE Transactions on Semiconductor Manufacturing* (ISSN 0894-6507), vol. 13, no. 2, May 2000, incorporated herein by reference. Controller 186 can include a microprocessor, microcontroller, programmable-logic device (PLD), programmable logic array (PLA), programmable array logic (PAL), field-programmable gate array (FPGA), application-specific integrated circuit (ASIC), or other computing or logic device programmed, wired, or configured to perform functions described herein. RGA controller 187 is connected to the equipment controller 186. RGA controller 187 or equipment controller 186 can also be connected to a host controller 188 via a communications link using, e.g., the SEMI Equipment Communications Standard (SECS) protocol. Host controller 188 or equipment controller 186, or both, can provide information to RGA controller 187. RGA controller 187 also controls, and collects information from, RGAs 120 and 121. In various aspects, equipment controller 186 and RGA controller 187 are two logic modules, subroutines, threads, or other processing components of a single controller.

In this document, buffer chamber 190 and transfer chamber 191 are referred to as "host" chambers. Host chambers have RGAs 120, 121. Chambers 101, 102, 103, and 104 are referred to as "guest" chambers or "guests" of transfer chamber 191. Chambers 113, 114, 115, 116, 118, and 119 are guests of buffer chamber 190. Chambers 111 and 112 can be referred to as guests of the transfer chamber 191 or the buffer chamber 190.

Various devices can be used for RGAs 120, 121. For example, an INFICON TRANSPECTOR XPR3 Gas Analysis System can measure atmospheres at pressures up to ~20 mTorr. This unit can detect leaks during pumpdown and sputtering. An open-ion-source RGA can be used to monitor during pumpdown, and a can operate at high vacuums, e.g., $10^{-7}$ Torr. In use, a process chamber (e.g., chamber 101 or chamber 113, or another guest chamber) can be held at certain pressure, e.g. 4 mTorr for 30 seconds to 2 to 3 minutes with a specified concentrations of selected gases in the chamber during the deposition process, then pumped down before moving the wafer to the buffer chamber.

Referring back to FIG. 1, in various aspects, RGAs 120, 121 are used to check for leaks for attached chambers in sequence. Leak checking and other measurements can be performed when the cluster tool is idle. In various aspects, leak-checking is done by executing a test recipe during tool idle that opens respective slit valves (e.g., slit valve 244, FIG. 2) on the guest chambers (e.g., chambers 101, 102) one-by-one, each for a certain time, and permits gases to diffuse into the corresponding host chamber (e.g., chamber 191) and be detected by the RGA therein (e.g., RGA 121). During the slide valve opening, other actions such as wafer pin lifts can be executed in order to detect leaks from the moving parts. These leaks can advantageously be detected by the RGA, but not by a standard ROR test, which does not move parts so as not to introduce pressure transients that decrease ROR accuracy.

For example, during tool idle, RGA 121 can be used to check for leaks in chambers 101, 102, 103, 104, and 112. RGA 120 can be used to check for leaks in chambers 113, 114, 115, 116, 111, and also chambers 118, 119. Each of chambers 113, 114, 115, 116, can be, e.g., a pre-clean or degas chamber. Each of chambers 101, 102, 103, 104 can be, e.g., a deposition chamber. Tests can be performed with different host chambers 190, 191 sequentially or simultaneously.

Figure 2:
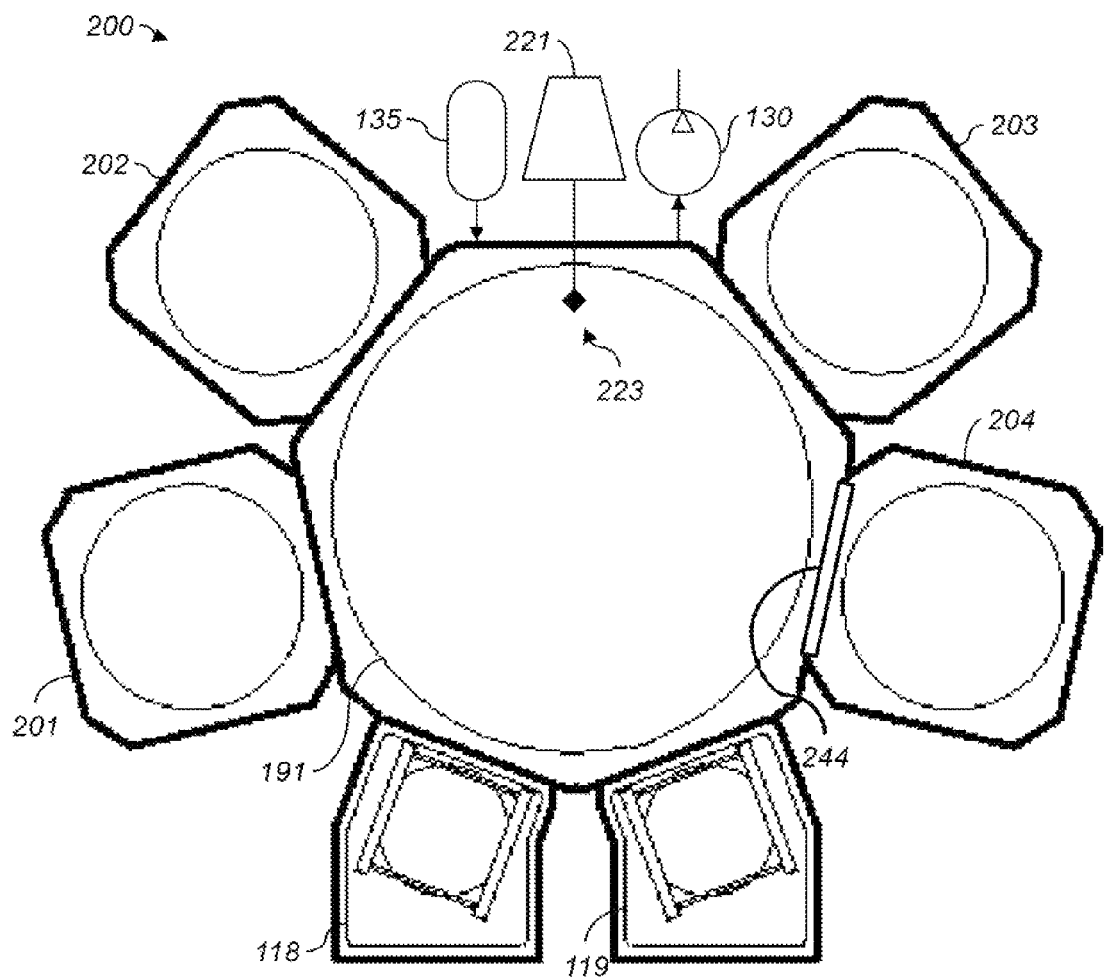

FIG. 2 shows an example of a vacuum tool, specifically a cluster tool 200, having two load-locks 118, 119, one transfer chamber 191, and four process chambers 201, 202, 203, 204. RGA 221, which can be a closed ion source RGA as discussed below, is used to measure the transfer chamber 191 using measurement probe 223, and corresponds to RGA 121 shown in FIG. 1. RGA 221 can be a closed ion source RGA such as the INFICON TRANSPECTOR CPM Compact Process Monitor. Gas can be supplied to the transfer chamber at a desired rate to maintain a selected pressure while wafers are transferred through the host chamber. Pump 130 is as shown in FIG. 1.

Slit valve 244 is shown between transfer chamber 191 and process chamber 204, and is represented graphically as a rectangle. A slit valve can be positioned between any pair of chambers in FIG. 1, 2, or 5; for clarity of the figures, other slit valves are not shown. Throughout this disclosure, chambers are referred to as being "coupled" when they are not isolated from each other. For example, chambers 191 and 204 are coupled when slit valve 244 is open but not when slit valve 244 is closed. The term "coupled" refers to the fact that the atmospheres of two coupled chambers can mix.

Cluster tool 200 can include or be operatively connected to a mainframe assembly (loadlocks, transfer chamber, process chambers) and an associated set of remote support equipment (RF power supplies, vacuum pumps, heat exchangers, computers). For example, various aspects can be used with an APPLIED MATERIALS CENTURA, a LAM RESEARCH 2300, a TOKYO ELECTRON TELIUS, or other tools. Process chambers 201, 202, 203, 204 can be configured for etching, chemical vapor deposition (CVD), thermal processing, or other processes. Gas supply 135 supplies desired atmospheric components to transfer chamber 191 while pump 130 is operating. In an example, gas supply 135 supplies argon (Ar) gas or nitrogen gas ($N_2$) so that transfer chamber 191 is filled with low-pressure argon or $N_2$ instead of with air. Tools can include 3-4 process chambers 201, 202, 203, 204 (guest chambers) around a single central transfer chamber 191 (host chamber) pumped down to ~10 mTorr. RGA 221 is used in that host chamber to measure all the process chambers 201, 202, 203, 204, as described herein. In various aspects, during wafer transfer, all chambers involved in the transfer, or all chambers in the tool, are pumped down with gas flow to set the composition and pressure of the atmosphere in the chambers. During tool idle, gas can be pumped through the chambers to maintain a selected atmosphere.

Figure 3:
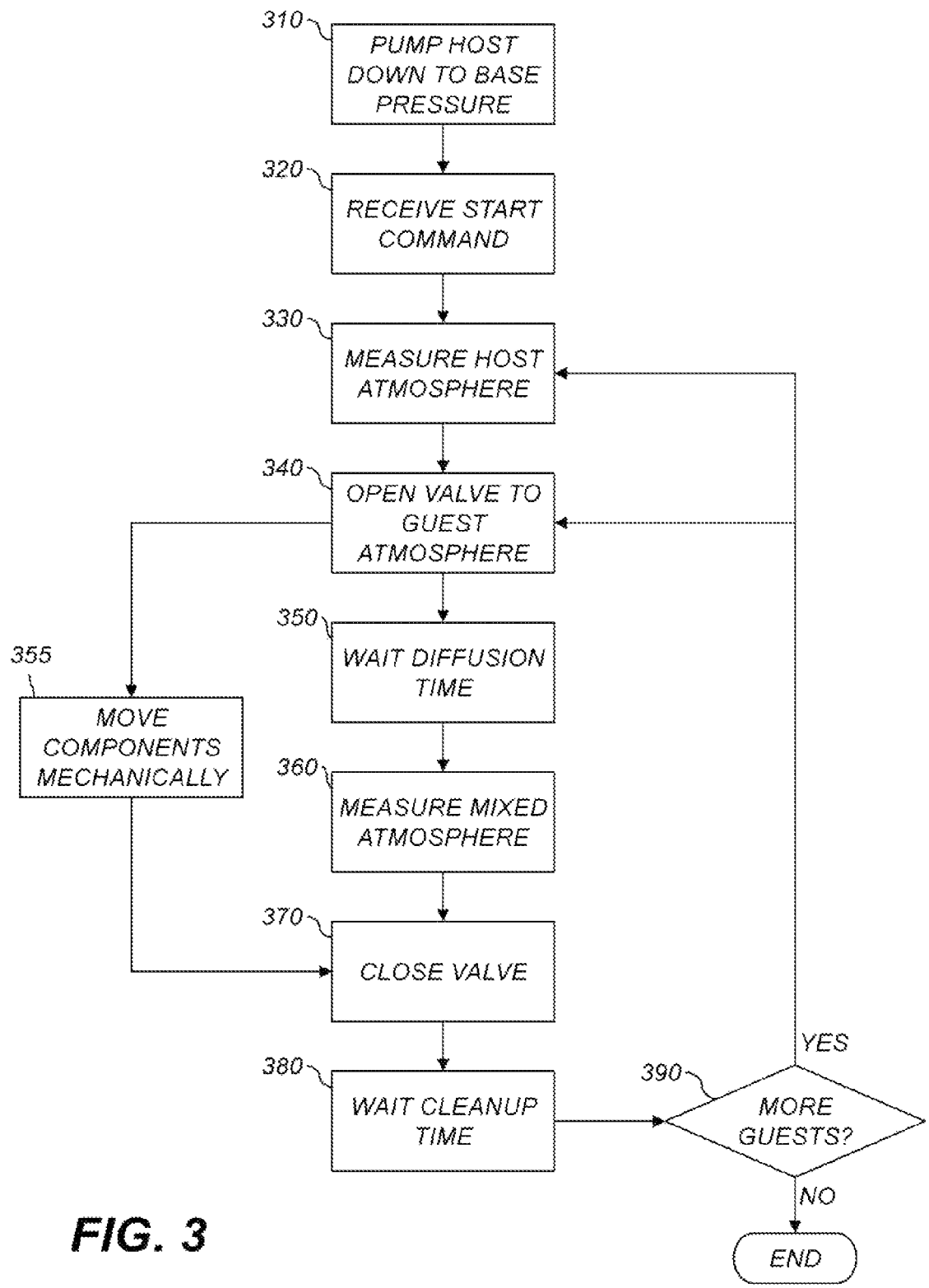
FIG. 3 shows examples of ways of measuring chambers according to various aspects.

FIG. 3 shows various examples of methods of measuring chambers. The steps in FIG. 3 can be performed in the order shown, or in other orders. Steps can be skipped. In an example, steps 310, 320, 330, 340, 350, 360, 370, 380, 390 are performed in that order. In another example, steps 310, 320, 330, 340, 350, 370, 360, 380, 390 are performed in that order. In various examples, steps 350, 355, 360 (or any two of those steps) are performed simultaneously, or in any relative order. For clarity of explanation, reference is herein made to various components shown in FIGS. 1 and 2 that can carry out or participate in the steps of the exemplary method. It should be noted, however, that other components can be used; that is, exemplary method(s) shown in FIG. 3 are not limited to being carried out by the identified components.

In step 310, a selected host chamber (e.g., chamber 190, 191) is pumped down to obtain a stable base pressure. Pump 130 can operate continuously, in which case step 310 includes waiting for the base pressure to be reached. In step 320, a start command is received. RGA controller 187 can wait for the start command before beginning the recipe. In various aspects, RGA controller 187 and equipment controller 186 communicate to sequence the tool operations, chamber openings, and RGA measurements to effectively measure the chambers.

In step 330, the host atmosphere is measured. The host atmosphere is the gas in the host chamber (e.g., chamber 191). Its pressure or compositions are measured with the corresponding RGA. This is done with the host chamber isolated from any attached guest chambers (e.g., chamber 101). For example, all the slit valves connecting the guests to the host (e.g., slit valve 244) can be closed during step 330.

In step 340, one of the slit valves (e.g., slit valve 244) is opened or other appropriate actions are taken to permit the host atmosphere (e.g., in transfer chamber 191, FIG. 2) and the guest atmosphere (e.g., in process chamber 204) to mix. The guest atmosphere is the gas in the guest chamber corresponding to the open slit valve.

In step 350, waiting is performed (e.g., no action is taken) during a diffusion time selected to permit the host and guest atmospheres to mix sufficiently. This mixture is referred to herein as a "mixed atmosphere." Since the pressures in the host and guest chambers are generally very low, the gas molecules in the respective atmospheres therein generally have long mean free paths. As a result, diffusion generally proceeds quickly. For example, for high vacuums of $10^{-5}$ Torr or lower pressure, the free path can be greater than 1m. Increasing the vacuum (reducing the pressure) can be useful for increasing the sensitivity of the RGA measurement.

In step 360, the mixed atmosphere is measured with the RGA in the host chamber. This can be done during step 350 or after, and with the slit valve open or closed (step 370). The measurements from step 330 are then subtracted from the measurements of this step 360 to infer the composition of the guest atmosphere. The guest atmosphere can include residual gases on the interested process chamber. Measurement of those residual gases permits determining the vacuum health of the guest chamber.

In various aspects relating to FIG. 2, transfer chamber 191 for tools such as that shown is maintained at a certain pressure, e.g. from hundreds of millitorr to tens of torr with a flow of either Ar or $N_2$ gas. A higher pressure has a shorter mean free path than a lower pressure, so it takes more time for gas diffusion from the guest chamber (e.g., process chamber 204) to the host chamber (e.g., transfer chamber 191). Therefore, step 360 can take longer for tools or chambers at higher pressure than for tools or chambers at lower pressures.

In step 370, the slit valve is closed. In step 380, waiting is performed until the host atmosphere has returned to a steady state, i.e., sufficient components of the guest atmosphere in the mixed atmosphere have been pumped out and replaced by host atmosphere. RGA measurements can be taken during step 380.

In decision step 390, it is determined whether there are more guest chambers to check. If so, the next step is step 330. In various aspects, RGA measurements are taken during step 380, and the next step is step 340. These aspects can be used in combination. Pumpdown can be performed before step 330 or step 340. RGA controller 187 can perform the waiting using a timer, and can take measurements and sequence slit valves. RGA controller 187, equipment controller 186, or both can include or be operatively connected to a memory that stores the recipe for measurements, and can sequence through that recipe. RGA controller 187 can provide instructions to equipment controller 186 to control the valves and other moving parts of the tool. Equipment controller 186 can provide control of the chamber slit valve and other moving parts of the tool and can also provide instructions to RGA controller 187 to control RGAs or RGA pneumatic valves if RGA pneumatic valves are installed. In some case, the RGA results such as air leak for a chamber can be sent to equipment controller 187 or host controller 188 (e.g., an industrial PC or HMI) for further action. RGA pneumatic valves can be used to control the flow of gas from the host chamber to the ion source of the RGA.

In various aspects, the method includes step 355, which can be carried out during steps 340, 350, 360, or 370, or any combination thereof. In step 355, one or more component(s) in the guest chamber or the host chamber are moved mechanically. For example, lift pins in the guest chamber can be moved through part or all of an operational cycle, or more than one cycle. This permits detecting leaks that only occur at a certain point during the motion of those parts. This particularly permits detecting such leaks that do not occur when the moving parts are in their idle or home positions.

Referring back to FIG. 1, in a comparative prior scheme, owing to the high pressure (e.g., 760 Torr) of chamber 118 when it is open to air for wafer transfer, there can be a pressure burst when the slit valve (not shown) of chamber 118 is opened to buffer chamber 190. In this comparative scheme, it is difficult to use the RGA in buffer chamber 190 for in-situ leak detection for process chambers (e.g., process chamber 113) on buffer chamber 190 between wafers or while the tool is operating due to the large pressure transients in the chambers. This restricts the ability of the comparative scheme to perform an "in-situ recheck" run every wafer.

In an inventive example, RGA controller 187 uses RGA 120 on buffer chamber 190 to check chambers 113, 114, 115, 116, and 111 in an ENDURA PVD tool while the tool is idle., e.g., between wafer lots, or as deemed necessary by the customer. Testing while idle is not subject to these large pressure transients. In various aspects, RGA testing of the guest chambers can be performed in less than 5 minutes and thus replace the current ROR test. In another example, RGA controller 187 uses RGA 121 on transfer chamber 191 to check chambers 101, 102, 103, 104, and 112 in an ENDURA.

In various aspects, using the RGA reduces sensitivity to pressure interference from other chambers or pressure noise from tool actions (such as robot arms moving). Therefore, RGAs on the buffer chamber 190 or the transfer chamber 191 can provide higher accuracy and sensitivity than ROR tests for process chamber air leak detection.

In various examples, process chambers 101, 102, 103, 104 are PVD, Metal Organic Chemical Vapor Deposition (MOCVD), CVD or Atomic Layer Deposition (ALD) deposition chambers. In various examples, chambers 113, 114 are etching-process chambers, e.g., Pre-clean II, Reactive Pre-clean, SICONI, or CVD/plasma etching. Chambers 113, 114 can also be CVD, MOCVD, or ALD process chambers. CVD can deposit metal (e.g., Ti) or organic materials. Process chambers can be attached to the buffer chamber 190 or the transfer chamber 191. Process chambers, e.g. deposition or etch process chambers, can be processing at certain pressure from several millitorr to several torr with the specified gas flow during the process, then they are pumped to base pressure, e.g. in an ENDURA tool, or maintain certain pressure with a gas flow, e.g. in a CENTURA tool.

Still referring to FIG. 1, in an example of an ENDURA PVD, the following exemplary recipe is used for tests with transfer chamber 191 as the host chamber:

A start command is received.
Transfer chamber 191 pumped down for 30 seconds to base pressure. RGA 121 can be run throughout this time, or periodically, or after this time expires.
Chamber 101 slit valve open for 15 seconds (or 10 seconds-1 minute, and likewise throughout). This permits diffusion between the host and guest atmospheres to form the mixed atmosphere. Since the mean free path of molecules under vacuum can be long, diffusion can be rapid. The pressure changes; in various examples, the amount of $H_2O$ in the atmosphere changes. The amount of $H_2O$ (outgassed from water remaining in a process chamber) can be lower in the chamber with better vacuum. RGA measurements can be taken during this time.
Chamber 101 slit valve closed; pump down back to transfer base pressure for 15 seconds.
Chamber 102 slit valve open for 15 seconds; take RGA measurement.
Chamber 102 slit valve closed; pump down back to transfer base pressure for 15 seconds.
Chamber 103 slit valve open for 15 seconds; take RGA measurement.
Chamber 103 slit valve closed; pump down back to transfer base pressure for 15 seconds.
Chamber 104 slit valve open for 15 seconds; take RGA measurement.
Chamber 104 slit valve closed; pump down back to transfer base pressure for 15 seconds.
Chamber 112 slit valve open for 15 seconds; take RGA measurement.
Chamber 112 slit valve closed; pump down back to transfer base pressure for 15 seconds.

Still referring to FIG. 1, in an example of an ENDURA PVD, the following exemplary recipe is used for tests with the buffer chamber 190 as the host chamber. The RGA 120 can be operated continually to take measurements. The exemplary recipe includes the following:

All chambers are pumped down to base pressure, e.g., $10^{-7}$ Torr or less.
A start command is received.
Buffer chamber 190 pumped down for 30 seconds (or 10 seconds—1 minute, as above). In various aspects, the buffer chamber is pumped to a high vacuum of $<10^{-7}$ Torr or $<10^{-6}$ Torr.
Pre-clean chamber 113 slit valve open for 15 seconds; take RGA measurement if desired.
Pre-clean chamber 113 slit valve closed; pump down back to buffer base pressure for 15 seconds. This step improves the accuracy of subsequent measurements by removing Pre-clean-C atmosphere from the host chamber (and likewise throughout).
Pre-clean chamber 114 slit valve open for 15 seconds; take RGA measurement.
Pre-clean chamber 114 slit valve closed; pump down back to buffer base pressure for 15 seconds.
Chamber 111 slit valve open for 15 seconds; take RGA measurement.
Chamber 111 slit valve closed; pump down back to buffer base pressure for 15 seconds.
Degas chamber 115 slit valve open for 15 seconds; take RGA measurement.
Degas chamber 115 slit valve closed; pump down back to buffer base pressure for 15 seconds.
Degas chamber 116 slit valve open for 15 seconds; take RGA measurement.
Degas chamber 116 slit valve closed; pump down back to buffer base pressure for 15 seconds.

In various aspects, a test recipe is run between each lot of wafers. This permits detecting failures before large numbers of wafers have been processed in a chamber needing corrective action. Wafers processed in such a chamber can be non-functional and thus less valuable. Reducing the number of lost wafers advantageously improves process yield and can lower manufacturing cost per die.

RGA tests of buffer chamber 190 or transfer chamber 191 can be performed at the same time or at different times. One of those tests can be performed without the other. In general, if air leaks in a PVD process chamber are of concern, the transfer chamber 191 can be tested using an RGA at the beginning of each lot of wafer processing or during wafer processing in the degas or pre-clean for the first or second wafers in a lot.

In various aspects, cleaner chambers are measured before dirtier chambers. For example, pre-clean chambers can be measured before degas chambers. This is because degas chambers can include hydrocarbon or photoresist contaminants that pre-clean chambers can be free of These contaminants can be difficult to pump away, so measuring degas after pre-clean reduces the probability of falsely indicating pre-clean chambers include those contaminants. The RGA can measure both pressure and composition, so selecting test order can improve result accuracy.

In an example, CVD or ALD process chambers are measured after PVD process chambers and after chamber B. CVD or ALD process chambers can be attached to buffer chamber 190 or transfer chamber 191.

Figure 4:
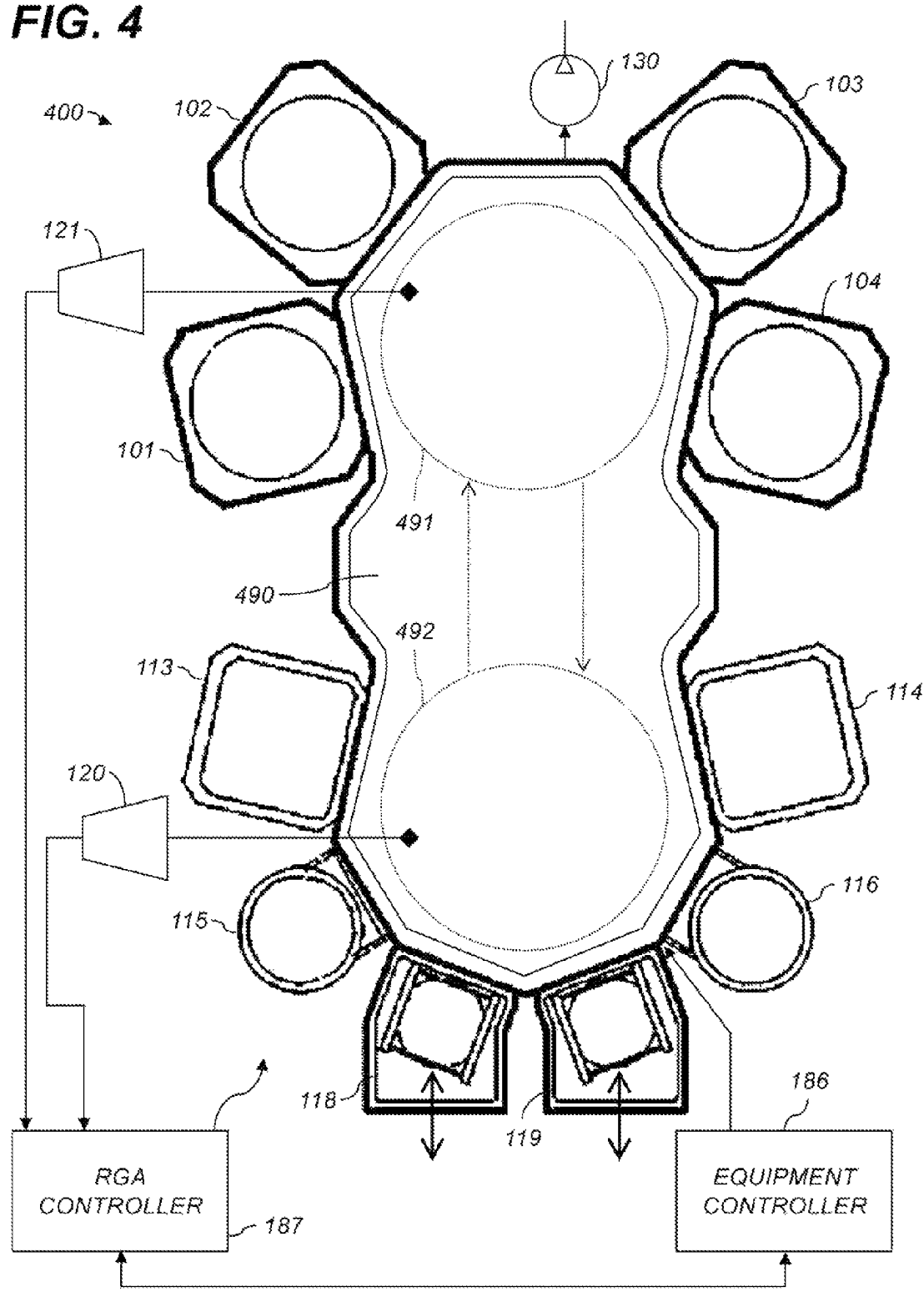
FIG. 4 is an example of a cluster tool according to various aspects.

FIG. 4 shows an exemplary cluster tool 400. Chambers 101, 102, 103, 104, 113, 114, 115, 116, 118, 119; equipment controller 186; RGA controller 187; RGAs 120, 121; and pump 130 are as shown in FIG. 1. Tool 400 has a single host chamber 490 to which chambers 101, 102, 103, 104, 113, 114, 115, 116, 118, 119 are connected, e.g., via slit valves (e.g., slit valve 244, FIG. 2). The probes of RGAs 120, 121 are both located in host chamber 490. RGA controller 187, equipment controller 186, or host controller 188 can compare the readings from RGAs 120 and 121 to investigate diffusion times in host chamber 490. Host chamber 490 can include one or more workcells 491, 492. Each workcell 491, 492 is an area of host chamber 490. The workcells 491, 492 freely share the atmosphere in host chamber 490 in the example shown. Each workcell 491, 492 can include a respective robot or actuator adapted to move wafers between adjacent chambers. In an example, a robot in workcell 491 can move wafers between chambers 101, 102, 103, and 104, and a robot in workcell 492 can move wafers between chambers 113, 114, 115, and 116, and load-locks 118, 119. The robots in workcells 491, 492 can exchange wafers with each other under control of equipment controller 186.

Cluster tools of this and similar configurations, and inline tools, can be used for flat-panel display (e.g., OLED or LCD) production. Host chamber 490 can have an area of, e.g., 6 m$^2$ or 8 m$^2$ (Gen 10 glass for LCD production). Host chamber 490 can be sized to hold a Gen 8.5 substrate having an area of 2.2 m×2.5 m, e.g., as used in LCD display fabrication, or a Gen 8 substrate.

Exemplary residual gas analyzers (RGAs) useful with various aspects described herein measure the individual partial pressures of gases in a mixture. An RGA system includes a probe that operates under high vacuum, electronics that operate the probe, and software working in conjunction with an external computer (not shown) to display data and control the electronics. The RGA includes an ion source, an analyzer, and a detector. The ion source emits electrons that collide with gas molecules in the vacuum system, giving them a net electrical charge, i.e., producing ions. This disclosure is not limited to any particular sign or magnitude of charge on the ions. The analyzer separates ions according to their mass-to-net-charge ratios. Mass is denoted "m" herein and net charge is denoted "z". References to "mass-to-charge" herein refer to the ratio of mass to net charge, i.e., m/z. The analyzer can include a linear quadrupole mass filter, a quadrupole analyzer other than a linear quadrupole mass filter, a magnetic-sector analyzer, an ion trap, or a time-of-flight analyzer.

Ions that have the selected mass-to-charge ratio pass through the analyzer to the detector, where they are neutralized at an electrode and draw a current that is proportional to—and thus identifies—the gas component present. Multiple gas components can be analyzed by successively operating the analyzer to sample different m/z ratios. For example, $CO_2^+$ has m/z=44, $N_2^+$ has m/z=28, and $O_2^+$ has m/z=32. Argon (Ar) has several isotopes, so measurements of an Ar atmosphere typically show some ions at m/z=36, fewer at m/z=38, and many more at m/z=40.

In an open ion source RGA, an ionization volume is maintained at the same pressure as the chamber being measured. The process gases in the chamber flow freely through the ionization volume, where some molecules are struck by electrons to form ions. In a closed ion source RGA, the ionization volume is only open to the process chamber through a small orifice, and a pump draws vacuum to reduce the pressure in the analyzer and the ion detector below the pressure in the ionization volume. This permits measuring chambers at higher pressures than the operating pressure of the quadrupole filter. Further details of ion sources are given in the above-referenced U.S. Pat. No. 5,850,084.

Examples of detectors include Faraday cups and electron multipliers. For example, ions striking a Faraday cup deposit their charge thereon, displacing corresponding charge to flow as a current along a readout electrode. In a channel electron multiplier, a high DC voltage is impressed across a cone to attract ions. Each positive ion impact inside the cone releases more electrons. Electrons travel from the cone down a channel to a readout electrode.

Other examples of residual gas analyzers and measurement techniques that can be used with various embodiments are given in US20030008422A1, entitled "Detection of nontransient processing anomalies in vacuum manufacturing process", published Jan. 9, 2003; U.S. Pat. No. 6,468,814B1, entitled "Detection of nontransient processing anomalies in vacuum manufacturing process", published Oct. 22, 2002; U.S. Pat. No. 6,740,195B2, entitled "Detection of nontransient processing anomalies in vacuum manufacturing process", published May 25, 2004; US20050256653A1, entitled "Inter-process sensing of wafer outcome", published Nov. 17, 2005; U.S. Pat. No. 7,257,494B2, entitled "Inter-process sensing of wafer outcome", published Aug. 14, 2007; US20090014644A1, entitled "IN-SITU ION SOURCE CLEANING FOR PARTIAL PRESSURE ANALYZERS USED IN PROCESS MONITORING", published Jan. 15, 2009; U.S. Pat. No. 5,850,084A, entitled "Ion lens assembly for gas analysis system", published Dec. 15, 1998; U.S. Pat. No. 5,889,281A, entitled "Method for linearization of ion currents in a quadrupole mass analyzer", published Mar. 30, 1999; U.S. Pat. No. 5,808,308A, entitled "Dual ion source", published Sep. 15, 1998; US20050258374A1, entitled "Replaceable anode liner for ion source", published Nov. 24, 2005; US20020153820A1, entitled "Apparatus for measuring total pressure and partial pressure with common electron beam", published Oct. Oct. 24, 2002; U.S. Pat. No. 4,692,630A, entitled "Wavelength specific detection system for measuring the partial pressure of a gas excited by an electron beam", published Sep. 8, 1987; U.S. Pat. No. 4,988,871A, entitled "Gas partial pressure sensor for vacuum chamber", published Jan. 29, 1991; U.S. Pat. No. 6,642,641B2, entitled "Apparatus for measuring total pressure and partial pressure with common electron beam", published Nov. 4, 2003; USRE38138E1, entitled "Method for linearization of ion currents in a quadrupole mass analyzer", published Jun. 10, 2003; and U.S. Pat. No. 7,041,984B2, entitled "Replaceable anode liner for ion source", published May 9, 2006, the disclosure of each of which is incorporated herein by reference.

Figure 5:
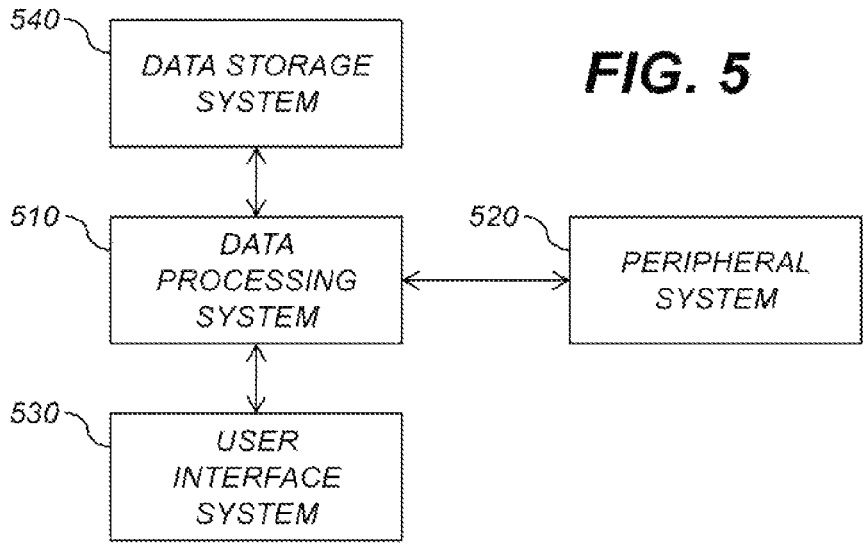
FIG. 5 is a high-level diagram showing the components of a data-processing system useful with various aspects.

FIG. 5 is a high-level diagram showing the components of a data-processing system for analyzing data and performing other analyses described herein. The system includes a data processing system 510, a peripheral system 520, a user interface system 530, and a data storage system 540. The peripheral system 520, the user interface system 530 and the data storage system 540 are communicatively connected to the data processing system 510. RGA controller 187, equipment controller 186 and receiver 130 can each include one or more of systems 510, 520, 530, 540.

The data processing system 510 includes one or more data processing devices that implement the processes of the various aspects, including the example processes described herein. The phrases "data processing device" or "data processor" are intended to include any data processing device, such as a central processing unit ("CPU"), a desktop computer, a laptop computer, a mainframe computer, a personal digital assistant, a Blackberry™, a digital camera, cellular phone, or any other device for processing data, managing data, or handling data, whether implemented with electrical, magnetic, optical, biological components, or otherwise.

The data storage system 540 includes one or more processor-accessible memories configured to store information, including the information needed to execute the processes of the various aspects, including the example processes described herein. The data storage system 540 can be a distributed processor-accessible memory system including multiple processor-accessible memories communicatively connected to the data processing system 510 via a plurality of computers or devices. On the other hand, the data storage system 540 need not be a distributed processor-accessible memory system and, consequently, can include one or more processor-accessible memories located within a single data processor or device.

The phrase "processor-accessible memory" is intended to include any processor-accessible data storage device, whether volatile or nonvolatile, electronic, magnetic, optical, or otherwise, including but not limited to, registers, floppy disks, hard disks, Compact Discs, DVDs, flash memories, ROMs, and RAMs.

The phrase "communicatively connected" is intended to include any type of connection, whether wired or wireless, between devices, data processors, or programs in which data can be communicated. The phrase "communicatively connected" is intended to include a connection between devices or programs within a single data processor, a connection between devices or programs located in different data processors, and a connection between devices not located in data processors. In this regard, although the data storage system 540 is shown separately from the data processing system 510, one skilled in the art will appreciate that the data storage system 540 can be stored completely or partially within the data processing system 510. Further in this regard, although the peripheral system 520 and the user interface system 530 are shown separately from the data processing system 510, one skilled in the art will appreciate that one or both of such systems can be stored completely or partially within the data processing system 510.

The peripheral system 520 can include one or more devices configured to provide digital content records to the data processing system 510. For example, the peripheral system 520 can include digital still cameras, digital video cameras, cellular phones, or other data processors. The data processing system 510, upon receipt of digital content records from a device in the peripheral system 520, can store such digital content records in the data storage system 540.

The user interface system 530 can include a mouse, a keyboard, another computer, or any device or combination of devices from which data is input to the data processing system 510. In this regard, although the peripheral system 520 is shown separately from the user interface system 530, the peripheral system 520 can be included as part of the user interface system 530.

The user interface system 530 also can include a display device, a processor-accessible memory, or any device or combination of devices to which data is output by the data processing system 510. In this regard, if the user interface system 530 includes a processor-accessible memory, such memory can be part of the data storage system 540 even though the user interface system 530 and the data storage system 540 are shown separately in FIG. 4.

In view of the foregoing, various aspects provide improved control by a person of data captured by surveillance systems that relates to that person. A technical effect is to provide a surveillance video stream that advantageously obscures people who do not which to be captured on video.

As will be appreciated by one skilled in the art, aspects of the present invention may be embodied as a system, method, or computer program product. Accordingly, aspects of the present invention may take the form of an entirely hardware aspect, an entirely software aspect (including firmware, resident software, micro-code, etc.), or an aspect combining software and hardware aspects that may all generally be referred to herein as a "service," "circuit," "circuitry," "module," and/or "system." Furthermore, aspects of the present invention may take the form of a computer program product embodied in one or more computer readable medium(s) having computer readable program code embodied thereon.

A computer program product can include one or more storage media, for example; magnetic storage media such as magnetic disk (such as a floppy disk) or magnetic tape; optical storage media such as optical disk, optical tape, or machine readable bar code; solid-state electronic storage devices such as random access memory (RAM), or read-only memory (ROM); or any other physical device or media employed to store a computer program having instructions for controlling one or more computers to practice method(s) according to various aspect(s).

Any combination of one or more computer readable medium(s) may be utilized. The computer readable medium may be a computer readable signal medium or a computer readable storage medium. A computer readable storage medium may be, for example, but not limited to, an electronic, magnetic, optical, electromagnetic, infrared, or semiconductor system, apparatus, or device, or any suitable combination of the foregoing. More specific examples (a non-exhaustive list) of the computer readable storage medium would include the following: an electrical connection having one or more wires, a portable computer diskette, a hard disk, a random access memory (RAM), a read-only memory (ROM), an erasable programmable read-only memory (EPROM or Flash memory), an optical fiber, a portable compact disc read-only memory (CD-ROM), an optical storage device, a magnetic storage device, or any suitable combination of the foregoing. In the context of this document, a computer readable storage medium may be any tangible medium that can contain, or store a program for use by or in connection with an instruction execution system, apparatus, or device.

Program code and/or executable instructions embodied on a computer readable medium may be transmitted using any appropriate medium, including but not limited to wireless, wireline, optical fiber cable, RF, or any suitable combination of appropriate media.

Computer program code for carrying out operations for aspects of the present invention may be written in any combination of one or more programming languages. The program code may execute entirely on the user's computer (device), partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider).

Computer program instructions can be stored in a computer readable medium that can direct a computer, other programmable data processing apparatus, or other devices to function in a particular manner. The computer program instructions may also be loaded onto a computer, other programmable data processing apparatus, or other devices to cause a series of operational steps to be performed on the computer, other programmable apparatus or other devices to produce a computer implemented process such that the instructions which execute on the computer or other programmable apparatus provide processes for implementing the functions/acts specified herein.

Figure 6:
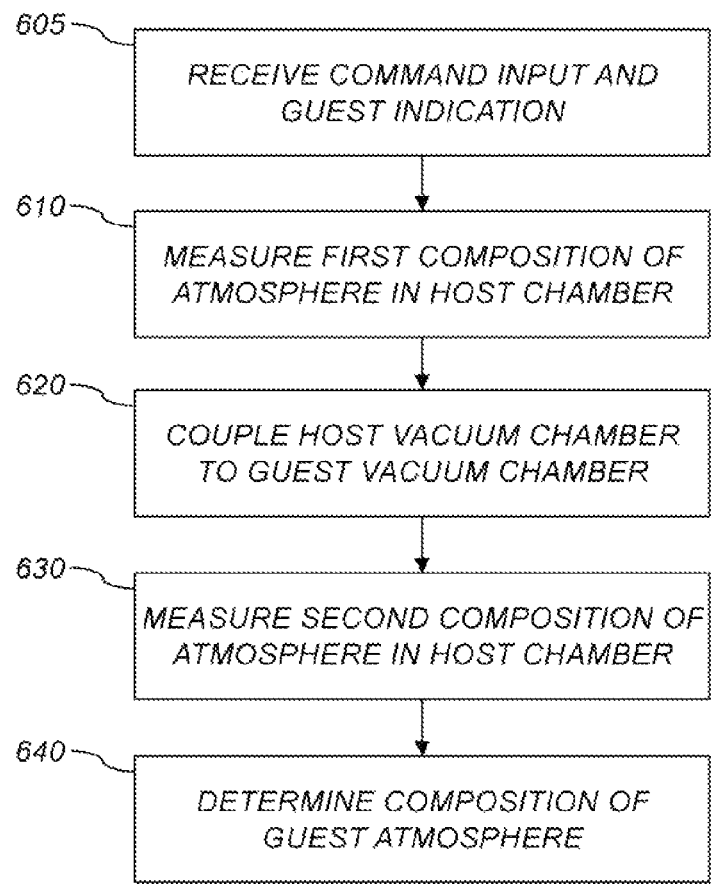
FIG. 6 shows a flowchart illustrating exemplary methods for measuring an atmosphere in a guest vacuum chamber of a vacuum tool.

FIG. 6 shows a flowchart illustrating an exemplary method for measuring an atmosphere in a guest vacuum chamber of a vacuum tool. The steps can be performed in any order except when otherwise specified, or when data from an earlier step is used in a later step. In at least one example, processing begins with step 610, or with step 605. For clarity of explanation, reference is herein made to various components shown in FIGS. 1-5 that can carry out or participate in the steps of the exemplary method. It should be noted, however, that other components can be used; that is, exemplary method(s) shown in FIG. 6 are not limited to being carried out by the identified components.

In step 605, a command input is received from a host interface. Steps 610, 620, 630, and 640, described below, are performed in response to the received command input. This can be done as discussed above with reference to step 320 (FIG. 3). In various aspects, the vacuum tool includes a plurality of guest vacuum chambers, e.g., chambers 201, 202, 203, 204 (FIG. 2). Step 605 includes receiving the command input and an indication of one of the plurality of guest vacuum chambers. The indication can be received from equipment controller 186. Steps 610, 620, 630, and 640 are performed in response to the received command input, and step 620 includes coupling the indicated one of the guest vacuum chambers to the host vacuum chamber.

In step 610, a first composition of an atmosphere in a host vacuum chamber 191 of the vacuum tool is measured using RGA 221 (both FIG. 2; part numbers are exemplary and not limiting). The host and guest vacuum chambers 191, 201 (respectively) are not coupled during the measuring of the first composition. This atmosphere can be referred to as a "host atmosphere." In various aspects, step 610 further includes pumping the host vacuum chamber 191 down to a selected pressure and concurrently measuring the atmosphere in the host vacuum chamber 191 using RGA 221.

In step 620, the host vacuum chamber 191 is coupled to the guest vacuum chamber 201. The atmosphere in the host vacuum chamber 191 mixes with an atmosphere in the guest vacuum chamber 201 (a "guest atmosphere") to form a mixed atmosphere in the host vacuum chamber 191. Step 620 can include coupling the chambers for at least 15 seconds.

In various aspects, a component within the host vacuum chamber 191 or the guest vacuum chamber 201 is mechanically moved while the host vacuum chamber 191 is coupled to the guest vacuum chamber 201. This is described above with reference to step 355 (FIG. 3). In various aspects, a selected time is permitted to elapse between the coupling step 620 and the measuring-second-composition step 630, discussed below. This can be done by programming equipment controller 186 or a processor such as data processing system 510 therein to wait for expiry of a software or hardware timer.

In step 630, after the chambers 191, 201 are coupled, a second composition of the atmosphere in the host vacuum chamber is measured using the RGA. is a measurement of the mixed atmosphere. The measurement of the first composition, e.g., as performed in step 610, is a measurement of the host atmosphere, as discussed above. The first and second compositions can be compared to determine the composition of the guest atmosphere as discussed herein, e.g., with respect to step 640. In various aspects, step 630 further includes pumping down the host vacuum chamber 191 after measuring the second composition.

In step 640, using a processor (e.g., controllers 186 or 187, FIG. 1, or system 510, FIG. 5), a composition of the guest atmosphere is automatically determined using the measured first and second compositions. For example, the measured RGA signals at various mass-to-charge ratios can be compared to determine what portion of the signal for each m/z is due to the guest atmosphere.

The invention is inclusive of combinations of the aspects described herein. References to "a particular aspect" and the like refer to features that are present in at least one aspect of the invention. Separate references to "an aspect" or "particular aspects" or the like do not necessarily refer to the same aspect or aspects; however, such aspects are not mutually exclusive, unless so indicated or as are readily apparent to one of skill in the art. The use of singular or plural in referring to "method" or "methods" and the like is not limiting. The word "or" is used in this disclosure in a non-exclusive sense, unless otherwise explicitly noted.

The invention has been described in detail with particular reference to certain preferred aspects thereof, but it will be understood that variations, combinations, and modifications can be effected by a person of ordinary skill in the art within the spirit and scope of the invention.

The invention claimed is:

1. A method of measuring an atmosphere in a guest vacuum chamber of a vacuum tool, the method comprising:
   pumping down a host vacuum chamber to a selected base vacuum pressure;
   measuring a first composition of an atmosphere in a host vacuum chamber of the vacuum tool using a residual gas analyzer (RGA) at the selected base vacuum pressure, wherein the host and guest vacuum chambers are not coupled during the measuring of the first composition;
   coupling the host vacuum chamber to the guest vacuum chamber, so that the atmosphere in the host vacuum chamber mixes with the atmosphere in the guest vacuum chamber to form a mixed atmosphere in the host vacuum chamber;
   measuring a second composition of the mixed atmosphere in the host vacuum chamber using the RGA after the chambers are coupled; and
   using a processor, automatically determining a composition of the atmosphere in the guest vacuum chamber using the measured first and second compositions.

2. The method according to claim 1, further including pumping down the host vacuum chamber to the selected base vacuum pressure after measuring the second composition.

3. The method according to claim 1, further including mechanically moving a component within the host vacuum chamber or the guest vacuum chamber while the host vacuum chamber is coupled to the guest vacuum chamber.

4. The method of claim 3, wherein the component is one or more lift pins arranged in the first guest vacuum chamber.

5. The method according to claim 1, further including automatically waiting a selected time between the coupling step and the measuring-second-composition step using the processor.

6. The method according to claim 1, wherein the selected base vacuum pressure is $10^{-7}$ Torr or less.

7. The method according to claim 1, further including receiving a command input from a host interface after pumping down the host vacuum chamber to the selected base vacuum pressure and performing the measuring-first-composition, coupling, measuring-second-composition, and determining steps in response to the received command input.

8. The method according to claim 1, wherein the vacuum tool includes a plurality of guest vacuum chambers and the method further includes receiving a command input and an indication of one of the plurality of guest vacuum chambers from an equipment controller and performing the measuring-first-composition, coupling, measuring-second-composition, and determining steps in response to the received command input, the coupling step including coupling the indicated one of the guest vacuum chambers to the host vacuum chamber.

9. The method according to claim 1, wherein the coupling step includes coupling the chambers for at least 15 seconds.

10. The method according to claim 1, wherein performing the measuring-first-composition, measuring-second-composition, and determining steps are performed when the vacuum tool is idle.

11. The method according to claim 1, further comprising the step of moving one or more lift pins arranged in the first guest vacuum chamber after the step of coupling the host vacuum chamber to the guest vacuum chamber and before the step of measuring a second composition of the mixed atmosphere in the host vacuum chamber.

12. A vacuum tool, comprising:
a first host vacuum chamber;
a first guest vacuum chamber;
a first valve operative to selectively couple the first host vacuum chamber and the first guest vacuum chamber;
a first residual gas analyzer (RGA) configured to measure composition of an atmosphere in the first host vacuum chamber; and
a processor configured to automatically operate the first valve to decouple the chambers, pump down the first host vacuum chamber to a selected base vacuum pressure, measure a first composition of the atmosphere in the first host vacuum chamber using the RGA at the selected base vacuum pressure, operate the first valve to couple the first host vacuum chamber and the first guest vacuum chamber so that the atmosphere in the first host vacuum chamber mixes with the atmosphere in the first guest vacuum chamber to form a first mixed atmosphere in the first host vacuum chamber, measure a second composition of the first mixed atmosphere in the first host vacuum chamber using the first RGA, and determine a composition of an atmosphere in the first guest vacuum chamber using the measured first and second compositions in the first host vacuum chamber.

13. The tool according to claim 12, further including one or more lift pins arranged in the first guest vacuum chamber, the processor further configured to move the lift pins while the chambers are coupled.

14. The tool according to claim 12, further including a second host vacuum chamber, a second guest vacuum chamber, a second valve operative to selectively couple the second host vacuum chamber to the second guest vacuum chamber, and a second RGA configured to measure composition of an atmosphere in the second host vacuum chamber, wherein the processor is further configured to automatically operate the second valve to decouple the second host chamber and the second guest chamber, pump down the first host vacuum chamber to a selected base vacuum pressure, measure a first composition of the atmosphere in the second host vacuum chamber using the second RGA at the selected base vacuum pressure, operate the second valve to couple the second host chamber and the second guest chamber so that the atmosphere in the second host vacuum chamber mixes with the atmosphere in the second guest vacuum chamber to form a second mixed atmosphere in the second host vacuum chamber, measure a second composition of the second mixed atmosphere in the host vacuum chamber using the second RGA, and determine a composition of an atmosphere in the second guest vacuum chamber using the measured first and second compositions in the second host vacuum chamber.

15. The tool according to claim 12, further including a second guest vacuum chamber and a second valve operative to selectively couple the host vacuum chamber and the second guest vacuum chamber, wherein the processor is configured to operate the first valve and the second valve so that only one of the first guest vacuum chamber and the second guest vacuum chamber is coupled to the first host vacuum chamber at any given time.

16. The tool according to claim 12, wherein the first host chamber includes a plurality of workcells.

17. The tool according to claim 12, wherein the first RGA is an open ion source RGA.

18. The tool according to claim 12, wherein the first RGA is a closed ion source RGA.

19. The tool according to claim 12, wherein the first valve is a slit valve.

20. The tool according to claim 12, further including a memory coupled to the processor and storing a recipe for measurements, wherein the processor is further configured to sequence through the stored recipe to determine the composition of the atmosphere in the first guest vacuum chamber.

* * * * *